US008926516B2

(12) United States Patent
Tsujino

(10) Patent No.: US 8,926,516 B2
(45) Date of Patent: Jan. 6, 2015

(54) ULTRASOUND IMAGING APPARATUS AND METHOD OF ULTRASOUND IMAGING

(75) Inventor: Hiroyuki Tsujino, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1200 days.

(21) Appl. No.: 11/109,629

(22) Filed: Apr. 20, 2005

(65) Prior Publication Data

US 2005/0245828 A1 Nov. 3, 2005

(30) Foreign Application Priority Data

Apr. 20, 2004 (JP) .................. 2004-124453

(51) Int. Cl.
*A61B 8/14* (2006.01)
*A61B 8/00* (2006.01)
*A61B 8/06* (2006.01)
*A61B 8/08* (2006.01)
*G01S 7/52* (2006.01)
*G01S 15/10* (2006.01)
*G01S 15/89* (2006.01)

(52) U.S. Cl.
CPC . *A61B 8/06* (2013.01); *A61B 8/481* (2013.01); *A61B 8/488* (2013.01); *G01S 7/52071* (2013.01); *G01S 7/52087* (2013.01); *G01S 15/102* (2013.01); *G01S 15/8961* (2013.01); *G01S 15/8979* (2013.01)
USPC ........................... 600/458; 600/453; 600/454

(58) Field of Classification Search
USPC ........... 600/458, 453–457, 437, 438; 382/128
See application file for complete search history.

(56) References Cited

U.S. PATENT DOCUMENTS

| 5,622,174 | A | | 4/1997 | Yamazaki |
| 5,724,976 | A | | 3/1998 | Mine et al. |
| 5,735,281 | A | * | 4/1998 | Rafter et al. .................. 600/458 |
| 5,827,204 | A | * | 10/1998 | Grandia et al. .................. 601/2 |
| 6,015,384 | A | * | 1/2000 | Ramamurthy et al. ....... 600/440 |
| 6,080,107 | A | * | 6/2000 | Poland ........................... 600/458 |
| 6,095,980 | A | * | 8/2000 | Burns et al. .................... 600/453 |
| 6,390,984 | B1 | * | 5/2002 | Pan et al. ....................... 600/453 |
| 6,450,961 | B1 | * | 9/2002 | Shiki et al. .................... 600/458 |
| 6,547,738 | B2 | * | 4/2003 | Lysyansky ..................... 600/458 |
| 2004/0010194 | A1 | * | 1/2004 | Kamiyama .................... 600/437 |

FOREIGN PATENT DOCUMENTS

JP 8-182680 7/1996

* cited by examiner

*Primary Examiner* — Katherine Fernandez
(74) *Attorney, Agent, or Firm* — Oblon, Spivak, McClelland, Maier & Neustadt, L.L.P.

(57) ABSTRACT

An ultrasound imaging apparatus comprises an ultrasonic probe configured to transmit and receive an ultrasonic wave and a controller configured to control the ultrasonic probe such that an ultrasonic wave for imaging a contrast agent injected into an object and an ultrasonic wave for imaging a tissue movement of the object are transmitted in time division. A method of ultrasound imaging comprises transmitting a first ultrasonic wave and a second ultrasonic wave which hardly destroys bubbles of a contrast agent, obtaining blood flow information based on a signal generated from the first ultrasonic wave, and obtaining tissue movement information based on a signal generated from the second ultrasonic wave.

17 Claims, 8 Drawing Sheets

ULTRASOUND IMAGING APPARATUS AND METHOD OF ULTRASOUND IMAGING

CROSS-REFERENCE TO RELATED APPLICATIONS

This application is based upon and claims the benefit of priority from prior Japanese Patent Application No. P2004-124453 filed on Apr. 20, 2004, the entire contents of which are incorporated herein by reference.

FIELD OF THE INVENTION

The present invention relates to an ultrasound imaging apparatus and a method of ultrasound imaging using an ultrasound wave.

BACKGROUND

It is very useful to evaluate quantitatively a motion (systole/diastole) of parts, such as a heart, when getting to know its function. For example, it is known that a wall-motion is changed in part, because of shortage of blood flow supplied from a coronary artery in ischemic heart disease. About the quantitative evaluation procedure of the partial wall motion, several methods, such as Tissue Doppler method or Tracking method of brightness of B mode image, have been proposed.

In the meanwhile, in order to know a status of the blood flow to cardiac muscle, a method for imaging a blood flow inside the cardiac muscle is clinically used. In this method, strong ultrasonic scatter characteristics in response to the contrast agent injected into an object is used.

In the method for imaging the contrast agent, there are mainly a High Mechanical Index (Hi-MI) method which uses a nonlinear signal generated from the contrast agent collapsed by a relatively high power ultrasound irradiation, and a Low-MI method which uses a signal generated from the contrast agent which is not collapsed by a relatively low power ultrasound irradiation. In the both methods, a signal from the tissue is reduced, and a signal from contrast agent, namely from the blood flow, is efficiently obtained.

For instance, Japanese Patent Disclosure (Kokai) No. 8-182680 discloses an ultrasound imaging apparatus for obtaining a contrast image using a nonlinear signal, and in order to separate a contrast agent signal and a tissue signal, a tissue Doppler image is obtained from a fundamental wave signal, and the contrast image and the tissue Doppler image are superimposed.

According to the method disclosed in the Japanese Patent Disclosure (Kokai) No. 8-182680, tissue functional information and blood flow information are obtained simultaneously. It is desired that the method contributes to a diagnosis when the blood flows but the wall does not move, which is so-called as a hibernation/swoon cardiac muscle.

In Japanese Patent Disclosure (Kokai) No. 8-182680, the tissue signal is obtained from the fundamental wave, however the following various problems may exist in actual situation when the contrast agent is injected to the patient.

First, since bubbles in the contrast agent are destroyed at the time of Hi-MI, wide band signals occur and phases of received signals become random. In such a situation, a speed also becomes random based on the signal detected in the Doppler method, and therefore, even if only the fundamental signal is used, an actual speed of the tissue is not assumed correctly.

Second, it is difficult to use Harmonic TDI (Harmonic Tissue Doppler Imaging) which is hardly influenced of a fixed noise and improves accuracy of the presumption of the speed. Especially, when the tissue signal is referred from the fundamental signal or the Low-MI is used, the non-linear signal is reduced.

Third, 1.5HI (Harmonic Imaging) is a contrast image method where only a signal from a bubble, which frequency is 1.5 times of the fundamental wave frequency, is efficiently extracted, not from a tissue Doppler. The tissue signal is canceled, and it is difficult to perform a tracking using the tissue information.

SUMMARY

One object of the present invention is to ameliorate the above-mentioned problems. For instance, in one aspect of the invention, a blood flow information and tissue movement information can be obtained when a contrast agent is injected.

According to one aspect of the present invention, there is provided an ultrasound imaging apparatus comprising an ultrasonic probe configured to transmit and receive an ultrasonic wave and a controller configured to control the ultrasonic probe such that an ultrasonic wave for imaging a contrast agent injected into an object and an ultrasonic wave for imaging a tissue movement of the object are transmitted in time division.

According to another aspect of the present invention, there is provided an ultrasound imaging apparatus comprising means for transmitting a first ultrasonic wave and a second ultrasonic wave which hardly destroy bubbles of a contrast agent, means for obtaining blood flow information based on a signal generated from the first ultrasonic wave, and means for obtaining tissue movement information based on a signal generated from the second ultrasonic wave.

According to another aspect of the present invention, there is provided an ultrasound imaging apparatus comprising means for transmitting a first ultrasonic wave, a second ultrasonic wave which destroys bubbles of a contrast agent and a third ultrasonic wave after the second ultrasonic wave, means for obtaining blood flow information based on a signal generated from the first ultrasonic wave, and means for obtaining tissue movement information based on a signal generated from the third ultrasonic wave.

According to another aspect of the present invention, there is provided an ultrasound imaging apparatus comprising means for transmitting a first ultrasonic wave for destroying most bubbles of a contrast agent and a second ultrasonic wave, after the first ultrasonic wave, used for detecting Doppler shift, means for obtaining blood flow information based on a non-linear signal generated from the first ultrasonic wave when the bubbles are destroyed, and means for obtaining tissue movement information based on a signal generated from the second ultrasonic wave.

According to another aspect of the present invention, there is provided a method of ultrasound imaging comprising transmitting a first ultrasonic wave and a second ultrasonic wave which hardly destroy bubbles of a contrast agent, obtaining blood flow information based on a signal generated from the first ultrasonic wave, and obtaining tissue movement information based on a signal generated from the second ultrasonic wave.

According to another aspect of the present invention, there is provided a method of ultrasound imaging comprising transmitting a first ultrasonic wave, destroying bubbles of a contrast agent and transmitting a second ultrasonic wave after destroying the bubbles of the contrast agent, obtaining blood flow information based on a signal generated from the first ultrasonic wave, and obtaining tissue movement information based on a signal generated from the second ultrasonic wave. In one embodiment, the bubbles are destroyed using a pressure wave, such as may be created by a third ultrasonic wave.

According to another aspect of the present invention, there is provided a method of ultrasound imaging comprises destroying most bubbles of a contrast agent, transmitting a first ultrasonic wave used for detecting Doppler shift, after destroying most of the bubbles of the contrast agent, obtaining blood flow information based on a non-linear signal generated from destroying most of the bubbles, and obtaining tissue movement information based on a signal generated from the first ultrasonic wave. In one embodiment, the bubbles are destroyed using a pressure wave, such as may be created by a second ultrasonic wave.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. In the drawings.

DETAILED DESCRIPTION OF EXEMPLARY EMBODIMENTS

Referring drawings, embodiments are explained below.

Figure 1:
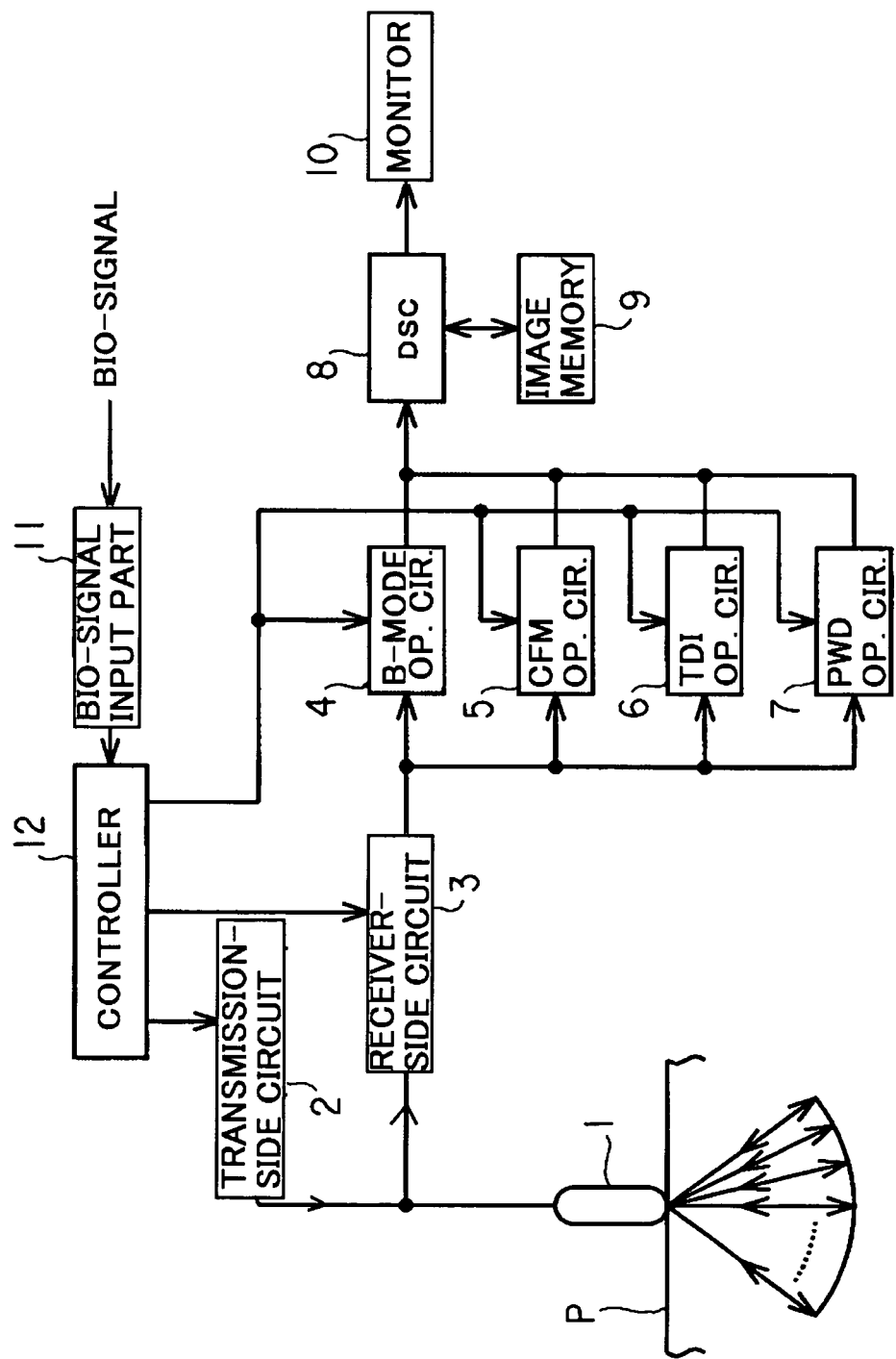
FIG. 1 is a block diagram of an Ultrasound imaging apparatus in a first embodiment.

In a first embodiment, FIG. 1 is a block diagram of an Ultrasound imaging apparatus. As shown in FIG. 1, the ultrasound imaging apparatus includes an ultrasonic probe 1, a transmission-side circuit 2, a receiver-side circuit 3, a B mode operation circuit 4, a CFM mode operation circuit 5, a TDI mode operation circuit 6, a PWD mode operation circuit 7, a digital scan converter (DSC) 8, an image memory 9, a monitor 10, a bio-signal input part 11, and a controller 12.

The ultrasonic probe 1 includes an array type piezoelectric vibrator arranged at the tip. The array type vibrator includes a plurality of piezoelectric elements arranged in a predetermined direction. Each piezoelectric element serves as a channel of transmission and reception, and a scanning is performed in the predetermined direction.

The ultrasonic probe 1 has a function of conversion between ultrasonic signals and electric signals. The ultrasonic probe 1 is connected to the transmission-side circuit 2 and the receiver-side circuit 3. The ultrasonic probe 1 may be an independent unit separated from a body part of the ultrasound imaging apparatus, and may be connected to the transmission-side circuit 2 and the receiver-side circuit 3 via a connector in use.

In this case, the body part and the ultrasonic probe 1 may be on a market as a single set or may be separately sold.

The transmission-side circuit 2 includes a pulse generator and a transmitting circuit. The pulse generator generates a basic rate pulse. The transmitting circuit makes the basic rate pulses delayed in each channel and generates driving pulses. The transmission-side circuit 2 supplies the driving pulses to the plurality of piezoelectric elements. Transmitting delay time of the driving pulse is controlled each channel, and the driving pulses are repeatedly supplied by each rate frequency.

According to the supply of the driving pulse, an ultrasonic pulse is generated from each piezoelectric element. The ultrasonic pulse transfers in the patient P and forms a transmitting beam according to the controlled delay time. The ultrasonic pulse is reflected on a border plane where sound impedance differs, and becomes an echo signal. The echo signal is received in part or all by one or more piezoelectric elements and is changed into a corresponding electric signal.

The receiver-side circuit 3 includes a preamplifier, a delay circuit and an adder. One preamplifier corresponds to one channel connected to the piezoelectric element of the ultrasonic probe 1. The preamplifier amplifies an analog electric signal corresponding to the echo signal received by the ultrasonic probe 1 by each channel. The delay circuit is connected to the preamplifier. One delay circuit corresponds to one preamplifier.

In order to focus a reception point, the delay circuit controls the delay time of the analog signal outputted from the preamplifier by each channel. The adder adds the analog signals from the channels after the delay control. Thus, the receiving beam which theoretically has the focal point determined according to control of reception delay time is formed, and desired directivity is obtained.

An output end of the receiver circuit 3 is connected to the B mode operation circuit 4, the CFM mode operation circuit 5, the TDI mode operation circuit 6, and the PWD mode operation circuit 7, in parallel.

The B mode operation circuit 4 generates monochrome tomographic image data of B mode and includes a logarithmic amplifier, an envelope wave detector, and an A/D converter. The logarithmic amplifier logarithmically compresses and amplifies the echo signal whose phase is adjusted to be added by the receiver-side circuit 3. The envelope wave detector detects an envelope of an output signal from the logarithmic amplifier. The A/D converter converts an output signal of the envelope wave detector into a digital signal. An output signal of the A/D converter is an output of the B mode operation circuit 4 as B mode image data.

The CFM mode operation circuit 5 includes a conventional circuit which detects blood flow information in two dimensions in Color Flow Mapping (CFM) that is a kind of a colored Doppler tomographic imaging method. The CFM mode operation circuit 5 includes a rectangular phase wave detector, an A/D converter, a MTI filer and a self-correction circuit. The CFM mode operation circuit 5 further includes an average speed operation circuit which operates based on an output of the self-correction circuit, a distribution operation circuit and a power operation circuit. The rectangular phase wave detector The rectangular phase wave detector detects a Doppler signal from the received echo signal. The A/D converter converts the detected Doppler signal into digital data. A frame memory in the MTI filter temporally stores the digital data outputted from the A/D converter.

In the CFM mode, in order to obtain the blood flow information, the same section is scanned several times. Therefore, the Doppler data includes three directional data in a beam scanning direction, a beam transmission direction and a time direction of the scanning. The MTI filter further includes a high pass filter in a readout side of the frame memory. Thus, a Doppler component in a tissue echo of a plurality of sets of the Doppler data, each of which is located at each pixel along the time direction of the scanning is removed, and a Doppler component of a blood-flow echo is appropriately extracted. The self-correction circuit analyzes an average Doppler frequency of the sets of Doppler data on which the high pass filtering is performed. The average speed operation circuit, the distribution operation circuit, and the power operation circuit calculate a blood-flow average speed of each sample point in the scanning section, a distribution value of a flow-velocity distribution and a power value of the echo signal from the blood flow based on the above-mentioned average Doppler frequency, respectively. The operation information is outputted from the CFM mode operation circuit 5 as colored Doppler information.

The TDI mode operation circuit 6 detects movement information of the tissue in two dimensions by Tissue Doppler Imaging (TDI) which is a kind of a colored Doppler tomographic imaging method. A composition of the TDI mode operation circuit 6 is similar to or the same as that of the CFM mode operation circuit 5 mentioned above, however characteristic of a filter circuit in a MTI filter is determined so that a Doppler component of the echo signal from the tissue of cardiac muscle etc. is extracted. That is, the characteristic is determined using difference in intensity and Doppler shift frequency (movement speed) between the tissue echo signal and the blood flow echo signal. Although the intensity of the tissue echo signal is relatively larger than that of the blood flow echo signal, the Doppler shift frequency (movement speed) is small in general. Therefore, the filter circuit in the MTI filter includes a low pass filter which extracts low Doppler shift frequency. Other composition is similar to or the same as that of the CFM mode operation circuit 5.

The PWD mode operation circuit 7 has a function to create Doppler spectrum data based on Pulsed-Doppler (PWD) method. Specifically, the PWD mode operation circuit includes a rectangular phase wave detector, a sample hold circuit, a band pass filter, an A/D converter, a FFT, etc.

The DSC 8 reconstructs an image from the signal outputted from each operation circuits 4 to 7. Moreover, the DSC 8 has a function to create an image for simultaneously displaying sets of information acquired in a plurality of modes by using the image memory 9.

The monitor 10 displays the image created by the DSC 8.

A bio-signal, such as an electrocardiogram (ECG) signal, is inputted with bio-signal input part 11 from outside.

The controller 12 includes a CPU. The controller 12 controls change of a sequence of pulse transmission and change of the mode.

Next, operation of the ultrasound imaging apparatus is explained. Since operation for obtaining information of the patient using the ultrasonic wave, operation for reconstructing an image from the acquired information are similar to or the same as a conventional ultrasound imaging apparatus, detailed explanation is omitted here. Since one feature of the embodiment is related to a sequence to obtain the blood-flow information and tissue movement information, the sequence is explained in detail below. The mode which obtains the blood-flow information and tissue movement information in parallel is called Contrast/TDI simultaneous mode.

The ultrasonic probe 1 is contacted to the patient P, and imaging by ultrasonic wave starts. The contrast agent is injected in to the patient P, and the contrast agent reaches its heart in dozens of seconds. Then, the Contrast/TDI simultaneous mode starts.

Figure 2:
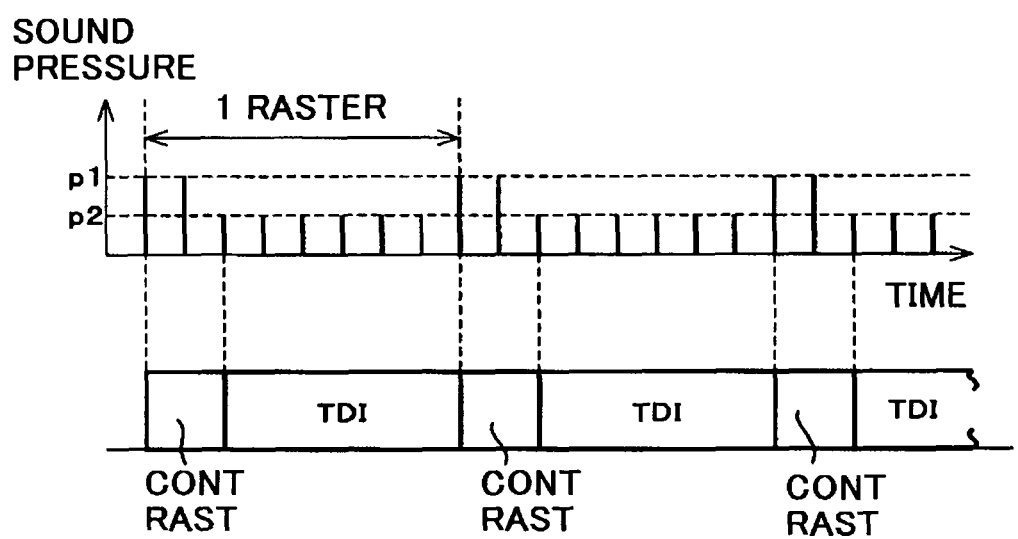
FIG. 2 is an illustration showing a sequence at Contrast/TDI simultaneous Mode in the first embodiment.

FIG. 2 shows a sequence in the Contrast/TDI simultaneous mode in the first embodiment. In FIG. 2, the upper portion shows a sequence of pulse transmissions and the lower portion shows a sequence of operation of information acquisitions.

In the Contrast/TDI simultaneous mode, the controller 12 performs the contrast mode and the TDI mode in turn during one raster period. The controller 12 drives the ultrasonic probe 1 so that an ultrasonic pulse of pressure p1 for contrast is transmitted at least once in an early stage of one raster period. In FIG. 2, the p1 pressure transmission is repeated twice per raster period. As shown in the lower portion of FIG. 2 in the sub-interval labeled "CONT RAST," under the control of the controller 12, the B mode operation is performed in the B mode operation circuit 4, using the nonlinear signal caused by the contrast agent according to the ultrasonic p1 pressure pulse. The B mode operation may be performed in any of the Hi-MI method or the Low-MI method. In FIG. 2, an example which uses the Hi-MI method and in which sound pressure p1 of the ultrasonic pulse for the contrast mode is set such that the bubbles of the contrast agent are destroyed. For example, the sound pressure p1 may be selected to be Mechanical Index 1.0, but other pressures are possible.

The controller 12 drives the ultrasonic probe 1 so that a sufficient number of other ultrasonic pulses are transmitted to enable TDI during the sub-interval labeled "TDI". For example, in FIG. 2, six additional ultrasonic pulses of pressure p2 for TDI are transmitted and their corresponding echos are measured. Sound pressure p2 of the ultrasonic pulse for TDI is low enough not to destroy the bubbles of the contrast agent. For example, the pressure p2 is Mechanical Index 0.1. As shown in the lower figure of FIG. 2, under the control of the controller 12, the TDI mode operation using a reflective wave of the ultrasonic pulse for the TDI is performed in the TDI mode operation circuit 6. Thus, a time divided signal of two pressures is applied by the probe 1.

Thus, in the contrast mode, highly precision blood-flow information can be obtained using the contrast agent. On the other hand, in the TDI mode, as the bubbles of the contrast agent are not destroyed, the tissue movement information is obtained using the reflective wave of the ultrasonic pulse for TDI. In a situation where the contrast agent is in the tissue of cardiac muscle etc., the speed of perfusion is lower than that of the cardiac muscle movement. Therefore, if the reflective wave of the ultrasonic pulse for TDI is presumed as a signal from the cardiac muscle in the TDI scanning, the speed of the tissue movement can be presumed in high precision.

In a second embodiment, most composition of an ultrasound imaging apparatus is similar to or the same as the first embodiment shown in FIG. 1. However, the second embodiment is different from the first embodiment in a control method of the controller 12 in the Contrast/TDI simultaneous mode. That is, a sequence in the Contrast/TDI simultaneous mode differs in the first embodiment and the second embodiment.

Figure 3:
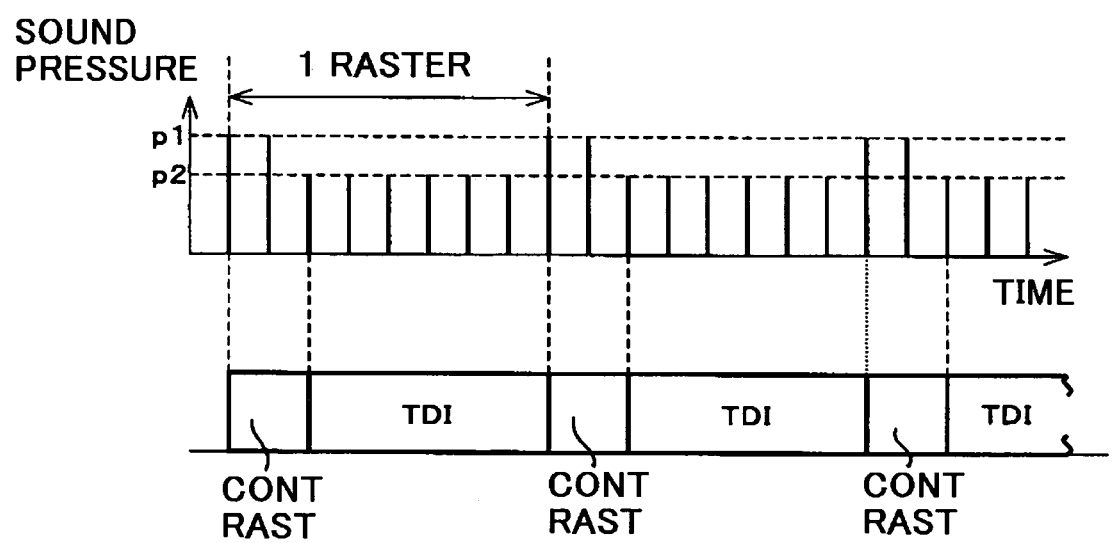
FIG. 3 is an illustration showing a sequence at Contrast/TDI simultaneous Mode in a second embodiment.

Hereafter, operation of the ultrasound imaging apparatus of the second embodiment is explained. FIG. 3 shows a sequence in the Contrast/TDI simultaneous mode of the second embodiment. In FIG. 3, the upper portion shows a sequence of pulse transmission and the lower portion shows a sequence of operation of information acquisition.

As shown in FIG. 3, the transmitting timing of the ultrasonic pulse and the execution timing of the B mode operation and TDI mode operation are similar to or the same as that of the first embodiment shown in FIG. 2.

However, in the second embodiment, under the control of the controller 12, sound pressure of the ultrasonic pulse for the contrast is set as high sound pressure p1, such as MI 1.6, which destroys most bubbles of the contrast agent on the raster. The ultrasonic pulse of the sound pressure MI 1.0 destroys most bubbles; however it is desirable that the sound pressure for Contrast is higher, such as MI 1.6, when the sound pressure for TDI is high, such as MI 1.0. That is, the ultrasonic pulse for the contrast is used also for destroying (Flashing) the bubbles. When the bubbles in the cardiac muscle temporally disappear, the ultrasonic pulse for TDI is transmitted. Thus, since the bubbles on the raster disappear when transmitting the ultrasonic pulse for TDI, the sound pressure p2 of the ultrasonic pulse for TDI can be set as the high sound pressure which may break bubbles, such as MI 1.0. Thereby, S/N of the TDI signal improves and highly precise tissue movement information can be obtained. Furthermore, since it is hardly influenced of the contrast agent, Harmonic TDI etc. may be used, and the tissue movement information is obtained in higher precision.

Figure 4:
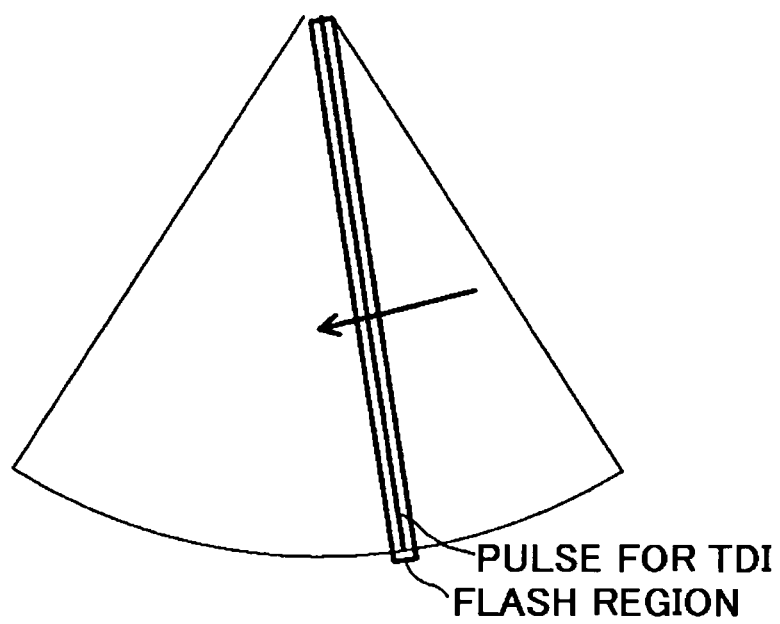
FIG. 4 is an illustration showing a flashing of a region covering a plurality of rasters.

However, peripheral bubbles may not disappear by the ultrasonic irradiation of one raster, and due to the movement of the heart, a region where the bubbles remain may be moved into a region of the raster when the ultrasonic wave for TDI is transmitted. As shown in FIG. 4, the flash may be executed on a region of a plurality of rasters and thereafter, the ultrasonic pulse for TDI may be transmitted. For example, when PRF (Pulse Repetition Frequency) is 1 kHz ($\Delta T=1$ ms), the number of TDI data samples (or measurements) is 10 and speed of the tissue movement is 100 mm/sec, the distance that the tissue moves during TDI scanning of one raster is 1 mm. In this case, if the bubbles are destroyed in a region of at least 1 mm width, the TDI information on the raster can be obtained. However, in consideration of motion of respiration etc., the flash may be executed on a region covering more rasters, and thereafter the TDI scanning may be performed.

In order that the ultrasonic pulse for contrast destroys bubbles, the Hi-MI method is applied in the contrast mode. The ultrasonic pulse of sound pressure p1 may be used only for the flashing. In this case, although simultaneous evaluation is not performed, it is possible to presume the speed of the tissue movement correctly even when the contrast agent injected. When the ultrasonic pulses for flash and for the contrast are transmitted in turn, the Low-Mi method may be used in the contrast mode.

In a third embodiment, most composition of an ultrasound imaging apparatus is similar to or the same as that of the ultrasound imaging apparatus of the first embodiment shown in FIG. 1. However, the third embodiment is different from the first embodiment in a control method of the controller 12 in the Contrast/TDI simultaneous mode. That is, a sequence in the Contrast/TDI simultaneous mode differs in the first embodiment and the second embodiment.

Figure 5:
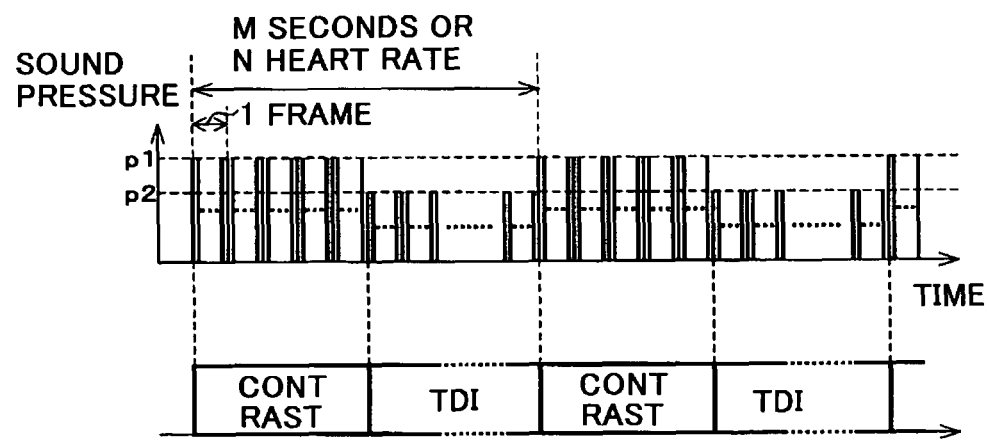
FIG. 5 is an illustration showing a sequence at Contrast/TDI simultaneous Mode in a third embodiment.

Hereafter, operation of the ultrasound imaging apparatus of the third embodiment is explained. FIG. 5 shows a sequence in the Contrast/TDI simultaneous mode of the third embodiment. In FIG. 5, the upper portion shows a sequence of pulse transmissions and the lower portion shows a sequence of operation of information acquisitions.

As shown in FIG. 5, in the third embodiment, sound pressure is not changed between rates but the contrast mode and the TDI mode are switched for each frame. In FIG. 5, the controller 12 uses the ultrasonic pulses through five rasters in the contrast mode. and each ultrasonic pulse has the high sound pressure to destroy most bubbles of the contrast agent on the raster. Thereafter, the controller 12 uses the ultrasonic pulses though a plurality of frames as the TDI mode, and each ultrasonic pulse has appropriate sound pressure p2 for the TDI. In this case, one cycle of the sequence is M seconds or N heartbeats. Utilizing several conditions, the M and N are determined.

For example, the flow velocity in a capillary blood vessel of cardiac muscle is about 1 mm/s. About 10 seconds are required until the blood flow is completely full again in a certain section (about 1 cm). Therefore, in order to perform TDI transmission without inflow of the bubbles, one cycle of the sequence is about 1 second (or at a specific timing every cardiac cycle), for example.

According to the third embodiment, since a burst (the contrast image) is reduced, it is possible to inhibit derogation of a frame rate. Consequently, it is possible to acquire efficiently the tissue movement information where time resolution is relatively important and the blood-flow information where time resolution is relatively unimportant.

In addition, also in the third embodiment, it may be adopted that the ultrasonic pulse for the contrast is different from the ultrasonic pulse for the flash.

In a fourth embodiment, most composition of an ultrasound imaging apparatus is similar to or the same as the first embodiment shown in FIG. 1. However, the fourth embodiment is different from the first embodiment in a control method of the controller 12 in the Contrast/TDI simultaneous mode. That is, a sequence in the Contrast/TDI simultaneous mode differs in the first embodiment and the second embodiment.

Figure 6:
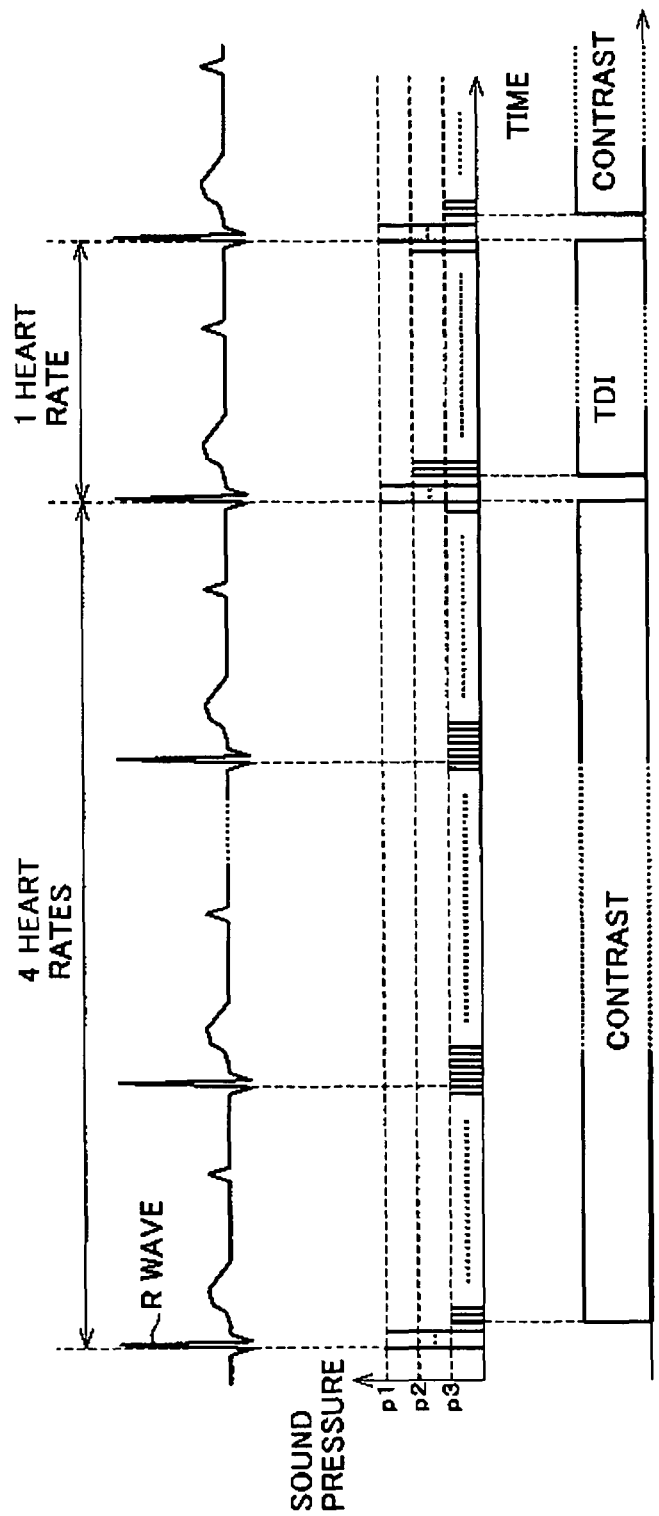
FIG. 6 is an illustration showing a sequence at Contrast/TDI simultaneous Mode in a fourth embodiment.

Hereafter, operation of the ultrasound imaging apparatus of the forth embodiment is explained. FIG. 6 shows a sequence in the Contrast/TDI simultaneous mode of the fourth embodiment. An upper figure of FIG. 6 shows an electrocardiogram signal inputted by the bio-signal input part 11 as a bio signal. A middle figure of FIG. 6 shows a sequence of pulse transmission, and a lower figure shows the sequence of operation of information acquisition.

As shown in FIG. 6, in the fourth embodiment, the contrast mode and the TDI mode are switched synchronizing with the electrocardiogram signal. In the example of FIG. 6, the controller 12 applies five heart beats to one cycle. A period of four heart beats in the cycle is applied to the contrast mode and the remaining period of one heart beat is applied to the TDI mode.

In a period of at least one frame after a first R wave appears on the electrocardiogram signal in the period of the contrast mode for the four heart beats, the controller 12 controls the transmitted ultrasonic pulse such that the sound pressure p1 is so high that the bubbles of the contrast agent on the raster are destroyed. Thereafter, while the controller 12 controls the transmitted ultrasonic pulse such that the sound pressure p3 is appropriate to the Low-MI method, the B mode operation circuit 4 performs the B mode operation by the Low-MI method.

In at least one frame after R wave appears in the electrocardiogram signal in the period for one heart beat for the TDI mode, the ultrasonic pulse of the sound pressure p1 is transmitted under control of the controller 12. Thereafter, while the controller 12 controls that the ultrasonic pulse is appropriate sound pressure p2 for the TDI, the TDI mode operation circuit 6 performs the TDI mode operation.

According to the fourth embodiment, the blood-flow information and the tissue movement information are collectable in high time resolution (i.e., at a high frame rate). However, since the blood-flow information and the tissue movement information which are not acquired in the same heart beat in this embodiment, it is desirable to perform time synchronization of the blood-flow information and the tissue movement information with reference to the electrocardiogram signal.

In addition, in the fourth embodiment, the Hi-MI method may be used in the contrast mode.

In the above embodiments, the acquisition of the highly precise blood flow information using the contrast agent and the acquisition of the highly precise tissue movement information by TDI are performed in parallel. By displaying both information simultaneously, it is possible to check the blood flow in the cardiac muscle (Perfusion) and a heart function (diastole and systole), which contributes to diagnosis for the ischemic heart disease, for example.

Figure 7:
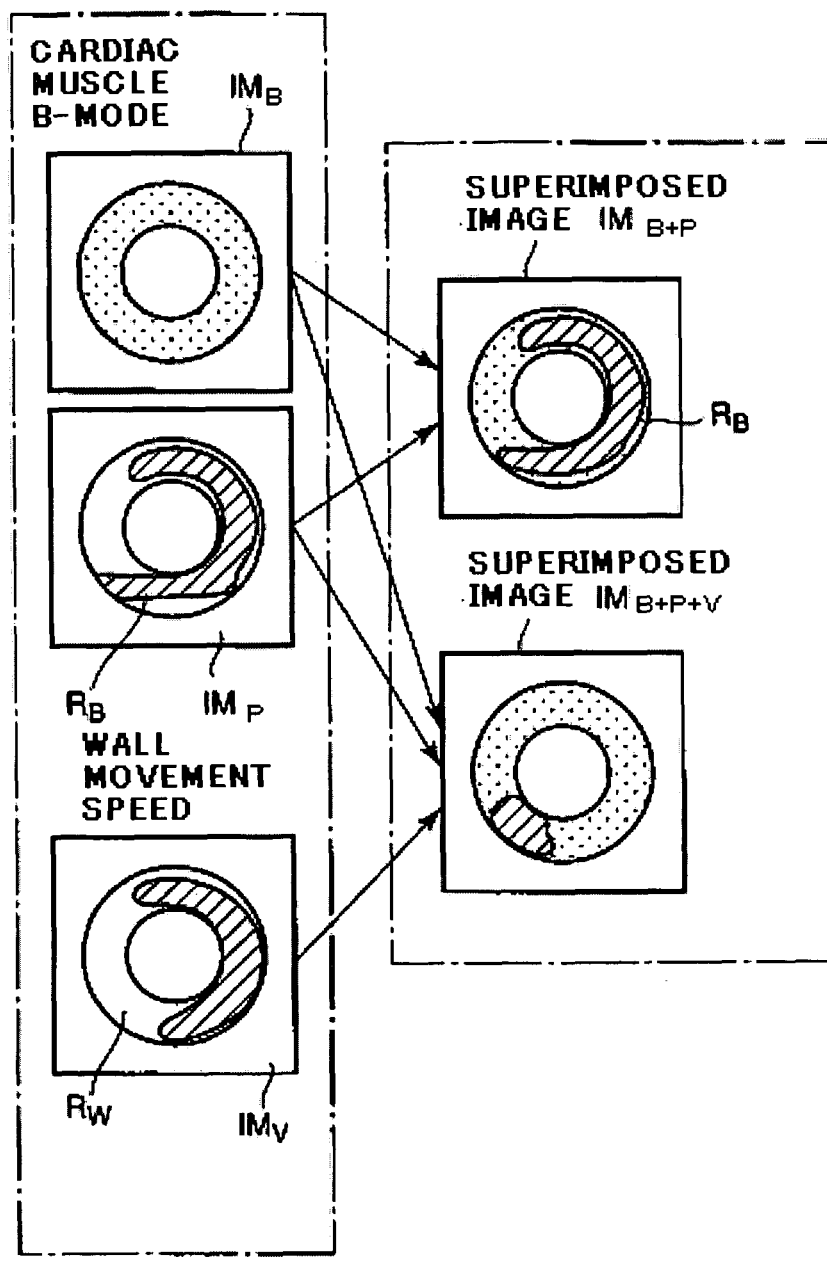
FIG. 7 is an illustration displayed in a multi image monitor in which blood information and tissue information are superimposed.

Several examples of effective display methods for diagnosis are explained below. FIG. 7 is an illustration displayed in the monitor 10 on which a superimposed image of the blood-flow information and the tissue movement information is displayed. In FIG. 7, the DSC 8 superimposes a B-mode image $IM_B$ based on the blood-flow information on a blood-flow distribution image (perfusion) $IM_P$ to display a superimposed image $IM_{B+P}$ on the monitor 10. The DSC 8 superimposes a 2-dimensional distribution image IMv based on tissue movement information on the B-mode image $IM_B$ and a blood-flow distribution image (perfusion) $IM_P$, and a superimposed image $IM_{B+P+V}$ is displayed on the monitor 10. A mark RB indicates a blood flow region and a mark RW indicates an usual movement region of a heart wall in FIG. 7.

Figure 8:
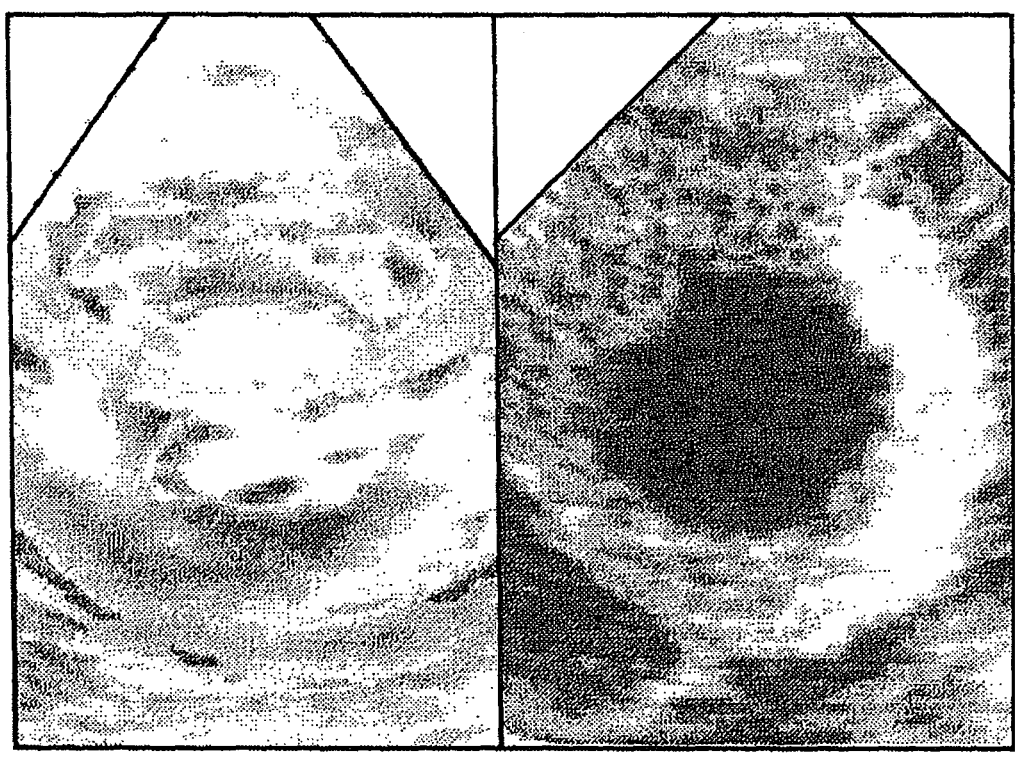
FIG. 8 is an illustration showing a middle gradation image indicating dual displayed images which are a perfusion image based on the blood information and a Doppler image based on the tissue movement information.

FIG. 8 shows a dual-display, middle gradation image in which the perfusion image is created based on the blood flow information and the Doppler image is created based on the tissue movement information. In FIG. 8, the perfusion image is located on a left side and the Doppler image is located on a right side.

In addition, as a single image, it may be possible to display a 2-dimensional color map in which a horizontal axis indicates a contrast power and a vertical axis indicates TDI speed, for example. According to the above embodiments, the blood-flow information is appropriately obtained using the contrast agent, and the tissue movement information is also appropriately obtained removing influence of the contrast agent, respectively.

In an alternate embodiment of FIG. 1, plural synchronized probes can be used. Moreover, a single probe with separate, independent connections to the transmission-side and receiving-side circuits can be utilized, or a single probe with shared connections to the transmission-side and receiving-side circuits can be utilized.

The present invention may be modified from the above embodiments without departing from the spirit or scope of the general inventive concept. It is therefore to be understood that within the scope of the appended claims, the present invention may be practiced differently than as specifically described herein. Although the above embodiment and modification may include various steps or various elements, one or more steps or elements may be arbitrarily selected. For instance, one or more steps or elements described as the embodiment or modification may be omitted. In addition, some elements in different embodiments may be combined. In the above mentioned embodiment, a Doppler shift method is used to detect the tissue movement information, however a pattern matching method may be used instead. In addition, for example, in FIG. 2, sound pressure p1 may be substantially equal to sound pressure p2 which is MI 1.0.

What is claimed is:

1. An ultrasound imaging apparatus, comprising:
    an ultrasonic probe configured to transmit and receive an ultrasonic wave; and
    a controller configured to control the ultrasonic probe to transmit a former ultrasonic wave whose ultrasonic pulse has a first sound pressure for imaging a contrast agent injected into an object and a latter ultrasonic wave whose ultrasonic pulse has a second sound pressure for Doppler imaging a tissue movement of the object in each of scan lines that form a scan region, wherein the first sound pressure and the second sound pressure are different and the second sound pressure is set so that most bubbles of the contrast agent injected into the object are not destroyed,
    wherein the controller is configured to control the ultrasonic probe to initially transmit the former ultrasonic wave to a first scan line of the scan lines, and transmit the latter ultrasonic wave to the first scan line at a predetermined timing that is after transmission of the former ultrasonic wave, before transmission of the former ultrasonic wave to each of the other scan lines, and before transmission of the latter ultrasonic wave to a second scan line of the scan lines, the second scan line being different from the first scan line.

2. The ultrasound imaging apparatus according to claim 1, further comprising an operation unit configured to obtain tissue movement information using a Doppler method.

3. The ultrasound imaging apparatus according to claim 1, further comprising an operation unit configured to obtain tissue movement information using a pattern matching method.

4. The ultrasound imaging apparatus according to claim 1, wherein the controller controls the ultrasonic probe to set the first sound pressure of the former ultrasonic wave for imaging the contrast agent so that most bubbles of the contrast agent are destroyed.

5. The ultrasound imaging apparatus according to claim 1, wherein the controller controls the ultrasonic probe to transmit an ultrasonic wave which destroys most contrast agent between transmissions of the former ultrasonic wave and the latter ultrasonic wave for Doppler imaging the tissue movement.

6. The ultrasound imaging apparatus according to claim 1, wherein the controller controls the ultrasonic probe to transmit an ultrasonic wave which destroys most contrast agent between transmissions of the former ultrasonic wave and the latter ultrasonic wave for Doppler imaging the tissue movement.

7. The ultrasound imaging apparatus according to claim 1, wherein the controller controls the ultrasonic probe to transmit the former ultrasonic wave and the latter ultrasonic wave for Doppler imaging the tissue movement in time division during a scan of a plurality of frames.

8. The ultrasound imaging apparatus according to claim 1, wherein the controller controls the ultrasonic probe to switch transmission of the former ultrasonic wave and transmission of the latter ultrasonic wave for Doppler imaging the tissue movement according to heart rate.

9. The ultrasound imaging apparatus according to claim 1, further comprising a display configured to display moving image information obtained based on the former ultrasonic wave and moving image information obtained based on the latter ultrasonic wave for Doppler imaging the tissue movement simultaneously.

10. An ultrasound imaging apparatus, comprising:
means for transmitting, in each of scan lines that form a scan region, a former ultrasonic wave having a first sound pressure and a latter ultrasonic wave having a second sound pressure which hardly destroys bubbles of a contrast agent, wherein the former ultrasonic wave and latter ultrasonic have different pressures and wherein the means for transmitting includes means for controlling an ultrasonic probe to initially transmit the former ultrasonic wave to a first scan line of the scan lines, and transmit the latter ultrasonic wave to the first scan line at a predetermined timing that is after transmission of the former ultrasonic wave, before transmission of the former ultrasonic wave to each of the other scan lines, and before transmission of the latter ultrasonic wave to a second scan line of the scan lines, the second scan line being different from the first scan line;
means for obtaining blood flow information based on a signal generated from the former ultrasonic wave; and
means for obtaining tissue movement information based on a signal generated from the latter ultrasonic wave.

11. An ultrasound imaging apparatus, comprising:
means for transmitting, in each of scan lines that form a scan region a first former ultrasonic wave, a second former ultrasonic wave and a latter ultrasonic wave after the second former ultrasonic wave which hardly destroys bubbles of a contrast agent, wherein said former ultrasonic waves and said latter ultrasonic wave have different pressures, at least one of the first former and second former ultrasonic waves being initially transmitted to a first scan line of the scan lines, and the latter ultrasonic wave being transmitted to the first scan line at a predetermined timing that is after transmission of the former ultrasonic wave, before transmission of the former ultrasonic wave to each of the other scan lines, and before transmission of the latter ultrasonic wave to a second scan line of the scan lines, the second scan line being different from the first scan line;
means for obtaining blood flow information based on a signal generated from the first former ultrasonic wave; and
means for obtaining tissue movement information based on a signal generated from the latter ultrasonic wave.

12. An ultrasound imaging apparatus, comprising:
means for transmitting, in each of scan lines that form a scan region, a former ultrasonic wave and a latter ultrasonic wave which hardly destroys bubbles of a contrast agent, after the former ultrasonic wave, used for detecting Doppler shift, wherein the former ultrasonic wave and the latter ultrasonic wave have different pressures the former ultrasonic wave being initially transmitted to a first scan line of the scan lines, and the latter ultrasonic wave being transmitted to the first scan line at a predetermined timing that is after transmission of the former ultrasonic wave, before transmission of the former ultrasonic wave to each of the other scan lines, and before transmission of the latter ultrasonic wave to a second scan line;
means for obtaining blood flow information based on a non-linear signal generated from the former ultrasonic wave when the bubbles are destroyed; and
means for obtaining tissue movement information based on a signal generated from the latter ultrasonic wave.

13. A method of ultrasound imaging, comprising:
transmitting, in each of scan lines that form a scan region, a former ultrasonic wave and a latter ultrasonic wave which hardly destroys bubbles of a contrast agent, wherein the former ultrasonic wave and the latter ultrasonic wave have different pressures, the former ultrasonic wave being initially transmitted to a first scan line of the scan lines, and the latter ultrasonic wave being transmitted to the first scan line at a predetermined timing that is after transmission of the former ultrasonic wave, before transmission of the former ultrasonic wave to each of the other scan lines, and before transmission of the latter ultrasonic wave to a second scan line of the scan lines, the second scan line being different from the first scan line;
obtaining blood flow information based on a signal generated from the former ultrasonic wave; and
obtaining tissue movement information based on a signal generated from the latter ultrasonic wave.

14. A method of ultrasound imaging, comprising:
transmitting, first, in each of scan lines that form a scan region, a former ultrasonic wave;
transmitting, secondly, in each of the scan lines that form the scan region, a latter ultrasonic wave which hardly destroys bubbles of a contrast agent, wherein the former ultrasonic wave and the latter ultrasonic wave have different pressures, the former ultrasonic wave being initially transmitted to a first scan line of the scan lines, and the latter ultrasonic wave being transmitted to the first scan line at a predetermined timing that is after transmission of the former ultrasonic wave, before transmission of the former ultrasonic wave to each of the other scan lines, and before transmission of the latter ultrasonic wave to a second scan line of the scan lines, the second scan line being different from the first scan line;
obtaining blood flow information based on a signal generated from the former ultrasonic wave; and
obtaining tissue movement information based on a signal generated from the latter ultrasonic wave.

15. The method as claimed in claim 14, further comprising destroying the bubbles of a contrast agent using an additional ultrasonic wave.

16. A method of ultrasound imaging, comprising:
transmitting, in each of scan lines that form a scan region, a former ultrasonic wave and a latter ultrasonic wave which hardly destroys bubbles of a contrast agent, after the former ultrasonic wave, used for detecting Doppler shift, wherein the former ultrasonic wave and the latter ultrasonic wave have different pressures, the former ultrasonic wave being initially transmitted to a first scan line of the scan lines, and the latter ultrasonic wave being transmitted to the first scan line at a predetermined timing that is after transmission of the former ultrasonic wave, before transmission of the former ultrasonic wave to each of the other scan lines, and before transmission of the latter ultrasonic wave to a second scan line of the scan lines, the second scan line being different from the first scan line;
obtaining blood flow information based on a non-linear signal generated from the former ultrasonic wave when the bubbles are destroyed; and
obtaining tissue movement information based on a signal generated from the latter ultrasonic wave.

17. A method of ultrasound imaging, comprising:
transmitting, in each of scan lines that form a scan region, former and latter ultrasonic waves, wherein the former ultrasonic wave and the latter ultrasonic wave have different pressures, the former ultrasonic wave being initially transmitted to a first scan line of the scan lines, and the latter ultrasonic wave being transmitted to the first scan line at a predetermined timing that is after transmission of the former ultrasonic wave, before transmission of the former ultrasonic wave to each of the other scan lines, and before transmission of the latter ultrasonic wave to a second scan line of the scan lines, the second scan line being different from the first scan line;

obtaining blood flow information based on a signal generated from the former ultrasonic wave; and obtaining tissue movement information based on a signal generated from the latter ultrasonic wave.

* * * * *